US007011964B2

(12) United States Patent
Bedford et al.

(10) Patent No.: US 7,011,964 B2
(45) Date of Patent: Mar. 14, 2006

(54) USE OF AN ENZYME FOR THE MANUFACTURE OF AN AGENT FOR CONTROLLING BACTERIAL INFECTION

(75) Inventors: Michael R. Bedford, Wiltshire (GB); Fresie Fernandez, Wiltshire (GB)

(73) Assignee: Finnfeeds International Ltd., Marlborough (GB)

(*) Notice: Subject to any disclaimer, the term of this patent is extended or adjusted under 35 U.S.C. 154(b) by 0 days.

(21) Appl. No.: 09/487,383

(22) Filed: Jan. 18, 2000

(65) Prior Publication Data
US 2001/0046494 A1    Nov. 29, 2001

Related U.S. Application Data

(63) Continuation of application No. PCT/EP98/04440, filed on Jul. 16, 1998.

(30) Foreign Application Priority Data
Jul. 18, 1997    (GB) ................................ 9715214

(51) Int. Cl.
   *C12N 9/00*    (2006.01)
(52) U.S. Cl. .................................................. 435/183
(58) Field of Classification Search ............. 424/94.61; 435/209
   See application file for complete search history.

(56) References Cited

U.S. PATENT DOCUMENTS

| 5,124,262 A |   | 6/1992  | Takasaki et al. |
|---|---|---|---|
| 5,314,692 A |   | 5/1994  | Haarasilta et al. ......... 424/94.2 |
| 5,470,725 A | * | 11/1995 | Borriss et al. ................ 435/93 |
| 5,612,055 A | * | 3/1997  | Bedford et al. ............. 424/442 |
| 5,624,678 A | * | 4/1997  | Bedford et al. ............. 424/442 |
| 5,817,500 A | * | 10/1998 | Hansen et al. .............. 435/200 |
| 5,902,581 A | * | 5/1999  | Clarkson et al. ......... 424/94.61 |

FOREIGN PATENT DOCUMENTS

| DE | 2617876    | 11/1976 |
|---|---|---|
| EP | 0195672    | 9/1986  |
| EP | 0681787    | 11/1995 |
| FR | 2448351    | 9/1980  |
| GB | 1503856    | 3/1978  |
| GB | 2261877    | 6/1993  |
| GB | 2287867    | * 10/1995 |
| JP | 9-84529    | 3/1997  |
| WO | 93/01800   | 2/1993  |
| WO | WO 93/13786 | 7/1993 |
| WO | WO 96/20709 | 7/1996 |
| WO | WO 97/29645 | 8/1997 |

OTHER PUBLICATIONS

"XP-002085479: Lysis of microorganisms by enzyme preparations and their components," 6001 Chemical Abstracts, Columbus, Ohio, US, vol. 104, No. 9, p. 329 (1986).

English Language Abstract of JP 81-73055.
Poultry Science, vol. 73, pp. 402-407 (1994).
Database WPI, Section Ch, Week 9723, Derwent Publications Ltd., London, GB; An 97-252948, XP002085480
Burrous, "Poultry Industry Quietly Cuts Back On Antibiotic Use—Major Change In Policy" appearing in The New York Times, Sunday, Feb. 10, 2002.
Schuff, "Reports Show Prevalence of Bacteria Contamination", Journal of Feedstuffs, vol. 74, No. 51, Dec. 16, 2002, pp. 1 and 22.
Fenster, "Feed Additives: A Global Market Study", Animal Pharm Reports, pp. 1-3 and 75-79, Jan. 30, 2001.
Bedford, "Removal of Antibiotic Growth Promoters From Poultry Diets: Implications and Strategies To Minimise Subsequent Problems", World's Poultry Science Journal, vol. 56, Dec. 2000, pp. 347-365.
Apajalahti et al., "Improve Bird Performance By Feeding Its Microflora", World Poultry, Elsevier vol. 15, No. 2, 1999, total of 3 pages.
Jones, "Why Chunky Chickens Are Better For Your Health", New Scientist, Mar. 24, 2001, total of 1 page.
Bedford, "Enzymes, Antibiotics And The Intestinal Microflora", Feed Mix, vol. 9, No. 2, 2001, pp. 32-34.
Fernandez et al., "Diet Influences The Colonisation Of *Campylobacter jejuni* And Distribution Of Mucin Carbohydrates In The Chick Intestinal Tract", Cell. Mol. Life Sci., 57 (2000) 1793-1801.
Tucker et al., "Feed Enzymes And Betain In Antibiotic Free Poultry Diets", AFMA Matrix, AFMA, PO Box 4473, Rivonia 2128, South Africa, Mar. 2000, vol. 9, No. 1, total of three pages.
Danisco Press Release, "Food Poisoning Bacteria *Campylobacter* and *Salmonella* Reduced In Broilers Fed Diets Supplemented with Enzyme", Aug. 2, 2002 total of 2 pages.
English Language Abstract of Aoyama Masakazu et al., "Effects of Water-Soluble Xylan prepared from Kumaizasa, Sasa Senanensis Rehd., on Multiplication of Human Intestinal Bacteria", Bamboo J., No. 11, pp. 29-35, Tbl. 5, Ref. 16 (1993).

* cited by examiner

*Primary Examiner*—Michael Meller
(74) *Attorney, Agent, or Firm*—Greenblum & Bernstein, P.L.C.

(57) ABSTRACT

Provided is the use of a xylanane or a cellulase for the manufacture of an agent for the treatment and/or prophylaxis of bacterial infection in an animal caused by *Salmonella*, *Campylobacter* or *Clostridium perfringens*.

It is preferred that xylanase is used in combination with wheat to form an animal feed. Such a diet is particularly effective in controlling *Campylobacter* and *Salmonella* in chickens.

The use provided by the present invention affords an alternative to antibiotics when controlling bacterial infection in animals. This leads to considerable health, environmental and economic benefits.

15 Claims, 13 Drawing Sheets

USE OF AN ENZYME FOR THE MANUFACTURE OF AN AGENT FOR CONTROLLING BACTERIAL INFECTION

This is a continuation of prior application number PCT/EP98/04440, filed 16 Jul. 1998 Designated the U.S., which is hereby incorporated herein by reference in its entirety.

BACKGROUND OF THE INVENTION

1. Field of the Invention

The present invention is directed to the use of an enzyme for the manufacture of an agent for the treatment and/or prophylaxis of a bacterial infection.

2. Discussion of Background Information

The farming of many different types of animals is important throughout the world for the production of food for human consumption. When the animals are reared, they come into contact with a variety of infection-causing bacteria, such as *Campylobacter* and *Salmonella*. In some cases these bacteria may spread directly from animals to humans (zoonosis). Accordingly, it is necessary from an economic, environmental and health perspective that such bacterial infection is prevented or eradicated in the animal prior to human consumption to prevent the spread of the disease to humans.

The domestic animal of particular, but not exclusive, concern with regard to zoonosis is the chicken. *Campylobacter* and *Salmonella* are particularly prevalent in the chicken. The bacteria are transmitted to the bird in a variety of ways, including through feed, water, litter and vermin. The bacteria initially infect the caecae of the chicken. The disease then progresses to the small intestine where infestation may cause loss of weight in the bird. A particular problem with the chicken is that it is almost impossible to eviscerate in a sterile manner with the result that bacteria inhabiting the intestines will invariably be transmitted to the saleable carcass. Accordingly the potential for zoonosis is great, unless the carcass is handled or cooked properly. The cost of human infection caused by eating improperly treated chicken is significant in terms of both time and lives.

Accordingly, presently there is a demand for improved methods of reducing bacterial infection in animals such as the chicken, in particular those intended for human consumption.

Various solutions to the problem of bacterial infection have been proposed. Current methods of control include the application of antibiotics, feed sterilisation and careful and controlled handling and cooking of the carcass after slaughter. Feed sterilisation has proved ineffective in the absence of a sterile rearing environment (which is impractical) whilst controlled handling and cooking cannot be relied upon in every instance. The application of antibiotics has proved unpopular with consumer groups wishing to reduce the quantity of potentially harmful chemicals in food. The use of antibiotics has the additional problem that if they are not introduced into the animal in a properly controlled manner, antibiotic-resistant strains of bacteria can be created, making such infections more difficult to treat in the future. The prophylactic use of antibiotics in animal feed has thus been regulated in some countries (notably Sweden and Finland) effectively reducing the available methods of control. Indeed no single method provides a barrier which completely prevents bacteria being transferred from the animal to humans.

As an alternative to the above methods it has been proposed in *Poultry Science*, 1994 73:402–407, to introduce flora into chickens to compete with the bacteria causing the infection. Such mucosal competitive exclusion flora (MCE) were found to reduce the level of *Campylobacter jejuni* infection in chickens. However, the competitive exclusion treatment is not found to be consistently effective, its efficacy varying from animal to animal.

JP-A-81-73055 discloses animal feeds intended to prevent contamination with *Salmonella*. The feeds are indicated to contain partially decomposed mannan in the form of mannose polysaccharides. These are produced by degradation of mannan with an enzyme, produced by micro-organisms. The resulting feed was found to be moderately effective against *Salmonella* in chickens, but is not effective against *Campylobacter*.

U.S. Pat. No. 5,124,262 discloses a mannose isomerase enzyme used for converting fructose to mannose. The mannose thus produced is taught to be useful in feeds, for inhibiting the growth of *Salmonella* in chickens.

In Bamboo J. 1993, pp. 29–35, xylan prepared from steamed bamboo grass is mentioned as inhibiting the growth of various human intestinal bacteria. In particular the xylan is indicated to be effective against *Salmonella*. However, the inhibition effect is reversed after a period of 24 hours.

The above methods have proved more desirable from an environmental and health point of view, than the administration of antibiotics. However, none have proved effective enough to be commercially viable.

WO 93/01800 discloses the use of a protease for the preparation of a medicament effective against intestinal pathogens in animals. The pathogens of interest include *Campylobacter*. However, there is no mention of enzymes other than proteases being useful in controlling animal pathogens.

EP-A-0 681 787 discloses use of a carbohydrase or protease for the manufacture of an agent for the treatment of Coccidiosis. However, Coccidiosis in chickens is caused by protozoal oocytes. The document does not indicate how bacterial pathogens in chickens, or other animals, can be controlled.

SUMMARY OF THE INVENTION

Accordingly, one object of the present invention is to provide an agent which can be used for controlling bacterial infection that is more effective than the presently available agents, and in particular than those described in the prior art acknowledged above. A further object of the present invention is to provide an agent which can be used for controlling bacterial infection that is less harmful to the environment, less expensive than the presently available agents, and has advantages for human health.

Accordingly, the present invention provides the use of a xylanase or a cellulase for the manufacture of an agent for the treatment and/or prophylaxis of bacterial infection in an animal caused by *Salmonella, Campylobacter* or *Clostridium perfringens*.

The present invention is directed to a method for reducing or eliminating antimicrobial drugs in the treatment and/or prophylaxis of bacterial infection in chickens caused by bacteria selected from the group consisting of *Salmonella, Campylobacter, Clostridium perfringens*, and mixtures thereof, the method comprising feeding the chickens a diet which diet is effective for the treatment and/or prophylaxis of bacterial infection in chickens caused by bacteria selected from the group consisting of *Salmonella, Campylobacter, Clostridium perfringens*, and mixtures thereof, the diet including xylanase with the xylanase being present in an amount effective for treatment and/or prophylaxis of the bacterial infection in the absence of an antimicrobial drug or in the presence of an antimicrobial drug at a concentration that is not effective for treatment and/or prophylaxis of bacterial infection in chickens caused by bacteria selected from the group consisting of *Salmonella, Campylobacter, Clostridium perfringens*, and mixtures thereof in the absence of the xylanase, and the diet not containing an antimicrobial drug or containing an antimicrobial drug at a concentration that is not effective for treatment and/or prophylaxis of bacterial infection in chickens caused by bacteria selected from the group consisting of *Salmonella, Campylobacter, Clostridium perfringens*, and mixtures thereof in the absence of the xylanase.

The present invention is also directed to a method for reducing or eliminating antimicrobial drugs in the treatment and/or prophylaxis of a bacterial infection in chickens caused by bacteria selected from the group consisting of *Salmonella, Campylobacter, Clostridium perfringens*, and mixtures thereof, the method comprising feeding the chickens a diet comprising a feed including a cellulase and at least about 25% by weight of a cereal selected from the group consisting of wheat, maize, rye, barley, oats, triticale, rice, sorghum and mixtures thereof, the diet being effective for treatment and/or prophylaxis of bacterial infection in the chickens caused by bacteria selected from the group consisting of *Salmonella, Campylobacter, Clostridium perfringens*, and mixtures thereof, and the cellulase being present in an amount effective for treatment and/or prophylaxis of the bacterial infection in the absence of an antimicrobial drug or in the presence of an antimicrobial drug at a concentration that is not effective for treatment and/or prophylaxis of bacterial infection in chickens caused by bacteria selected from the group consisting of *Salmonella, Campylobacter, Clostridium perfringens*, and mixtures thereof in the absence of the cellulase, and the diet not containing an antimicrobial drug or containing an antimicrobial drug at a concentration that is not effective for treatment and/or prophylaxis of bacterial infection in chickens caused by bacteria selected from the group consisting of *Salmonella, Campylobacter, Clostridium perfringens*, and mixtures thereof in the absence of the cellulase.

Still further, the present invention is directed to a method for reducing or eliminating antimicrobial drugs in the treatment and/or prophylaxis of a bacterial infection in chickens caused by bacteria selected from the group consisting of *Salmonella, Campylobacter, Clostridium perfringens*, and mixtures thereof, the method comprising feeding the chickens a diet comprising a feed including a β-glucanase and at least about 25% by weight of wheat, the diet being effective for treatment and/or prophylaxis of bacterial infection in the chickens caused by bacteria selected from the group consisting of *Salmonella, Campylobacter, Clostridium perfringens*, and mixtures thereof, and the β-glucanase being present in an amount effective for treatment and/or prophylaxis of the bacterial infection in the absence of an antimicrobial drug or in the presence of an antimicrobial drug at a concentration that is not effective for treatment and/or prophylaxis of bacterial infection in chickens caused by bacteria selected from the group consisting of *Salmonella, Campylobacter, Clostridium perfringens*, and mixtures thereof in the absence of the β-glucanase, and the diet not containing an antimicrobial drug or containing an antimicrobial drug at a concentration that is not effective for treatment and/or prophylaxis bacterial infection in chickens caused by bacteria selected from the group consisting of *Salmonella, Campylobacter, Clostridium perfringens*, and mixtures thereof in the absence of the β-glucanase.

The diet can be fed to the chickens without a withdrawal period prior to slaughtering of the chickens.

A preferred cellulase is β-glucanase.

DETAILED DESCRIPTION OF THE INVENTION

The advantage of using feeds containing a xylanase or a cellulase for rearing animals is that the amount of antimicrobial drugs which have previously been routinely incorporated into their diet can be reduced, or in some cases omitted entirely. This enables considerable economic savings to be achieved in view of the relative expense of antibiotics. In countries where such drugs are banned, it represents a totally new approach to the control of bacterial diseases.

When omitting antibiotics from an animal's diet there are several potential further benefits. It has previously been necessary to withdraw antibiotics from the animal's diet for a certain time prior to slaughter. This ensures that the meat is relatively free from such drugs and thus fit for human consumption. In contrast, if antibiotics are entirely omitted from an animal's diet, as may be achieved with the present invention, then the animal can be slaughtered at any age rather than after a certain withdrawal period. This affords the farmer improved flexibility and removes the risk of animals becoming infected shortly prior to slaughter. Further, meat and eggs can be guaranteed free of antibiotics. Such meat and eggs have a market advantage as compared to products which cannot support such a guarantee.

Even if the enzyme added to the animal's diet only enables the level of inclusion of antibiotics to be reduced, then the overall cost of controlling bacterial infection will be reduced. Synergy or potentiation may extend the useful life of the antibiotic.

The present invention also has benefits for human health. Its use reduces the selection pressure for antibiotic-resistant strains of bacteria, by allowing antibiotics to be removed from animal feed. Accordingly, more antibiotic-susceptible strains will be present in the gut of the animal, thereby ensuring a more likely positive outcome in the event of antibiotics being used on the equivalent human condition.

The xylanase or cellulase enzyme to be used in the feeds can be formulated as a pre-mix together with any other enzymes to be included. The pre-mix can be added to the raw materials before feed manufacture, during feed manufacture or as a final step once the feed is otherwise ready for use. It is possible to add the enzyme directly as a liquid to a feed material pre-formed as pellets or as a mash.

It is also possible to include the enzyme in the animal's diet by incorporating it into a second (and different) feed or drinking water which the animal also has access to. Accordingly, it is not essential that the enzyme is incorporated into the feed itself, although such incorporation forms a particularly preferred aspect of the present invention.

If the enzyme is incorporated into a feed, then this preferably comprises at least 25% by weight of a cereal, and more preferably at least 35% by weight of the cereal. The cereal may be any one or more of wheat, maize, rye, barley, oats, triticale, rice, and sorghum. It is particularly preferred that the cereal is wheat.

Although the cereal component of a cereal-based diet constitutes a source of protein, it is usually necessary to include sources of supplementary protein in the diet, such as those derived from fishmeal, meatmeal or vegetables. These sources of supplementary protein may constitute up to 50% by weight of the animal feed. Sources of vegetable protein include at least one of full fat soybean, rapeseed, canola, soybean meal, rapeseed meal and canola meal.

If the enzyme is incorporated into a feed, then this is preferably added in a relative amount of 0.0001–10 g of the enzyme per kilo of the feed, more preferably 0.001–1 g/kg and most preferably 0.01–0.1 g/kg.

The xylanase for use in this invention can be obtained from a fungus, such as *Trichoderma, Aspergillus, Humicola*, or *Neocallimastix*. Alternatively, the xylanase can be obtained from a bacterium, such as *Bacillus, Streptomyces, Clostridium*, or *Ruminococcus*.

The present invention is particularly effective against strains of *Salmonella* and *Campylobacter*, and especially *Salmonella enteritidis* and *Campylobacter jejuni*. Another bacterium against which the invention is effective is *Clostridium perfringens*.

Bacterial infection can be treated or prevented in accordance with the present invention in a wide variety of animals, but use of the invention is particularly preferred in domestic animals and farm livestock. Animals which may in particular benefit from the invention include poultry (such as chickens, turkeys, ducks and geese), ruminants (such as cattle, horses and sheep), swine (pigs), cats, dogs, rodents (such as rabbits) and fish. The invention is particularly useful in broiler chickens.

The most preferred combinations of feed and enzyme include wheat plus xylanase, maize plus xylanase and barley plus β-glucanase.

The enzymes used in the present invention fall within a general Class called polysaccharidases. Their substrates are structural polysaccharides such as xylans and β-glucans that occur as an integral part of the cell wall of most land plants. These polysaccharides are not found in animal cells, and are not to be expected to have any activity against proteins. Because these enzymes attack polysaccharides found in plant cell walls, the only possible substrates for these enzymes in the gastrointestinal tract of an animal are contained in cereal-based feeds. It is therefore speculated that the beneficial effects of the xylanase or cellulase on bacterial infection result somehow from the degradation products which they produce such as xylan or β-glucan derived from a cereal-based diet.

As previously mentioned, WO 93/01800 discloses the use of a protease for the preparation of a medicament effective against intestinal pathogens in animals. It is well established that such pathogens mediate their infectivity by binding to receptors on the surface of intestinal epithelial cells via antigenic protein or glycoprotein molecules expressed on the pathogen's cell surface. It is suggested that the protease enzyme prevents binding of the pathogen cells to the intestinal epithelium by destroying these proteinaceous receptor/adhesion sites to which the pathogen must bind if it is to cause an infection. The protease enzymes mentioned in this reference would be predicted to destroy proteins on the lumenal surface of intestinal epithelial cells in a non-specific manner, but would not be expected to attack substrates other than proteins. Accordingly, the activity of the proteases disclosed in this reference is fundamentally different from the activity of the enzymes used in the present invention. A skilled person could not have predicted the utility of the present enzymes against bacterial infection based upon the activity of proteases disclosed in WO 93/01800.

The invention will now be described in more detail according to the following Examples.

EXAMPLES

General Methodology

Wheat and maize diets were prepared having the following formulations:

TABLE 1

| Wheat diet | |
|---|---|
| Ingredients | Percent |
| Soft Wheat | 58.83 |
| Soybean ml 48 | 32.49 |
| Soy oil | 4.49 |
| Salt | 0.30 |
| Sodium Bicarbonate | 0.12 |
| DL Methionine | 0.14 |
| Limestone | 1.37 |
| Di-calcium Phosphate | 1.26 |
| Vitamins/Minerals | 1.00 |
| TOTAL | 100.00 |

TABLE 2

Maize diet

| Ingredients | Percent |
| --- | --- |
| Maize | 55.38 |
| Soybean ml 48 | 37.30 |
| Soy oil | 2.96 |
| Salt | 0.30 |
| Sodium Bicarbonate | 0.16 |
| DL Methionine | 0.13 |
| Limestone | 1.22 |
| Di-calcium Phosphate | 1.55 |
| Vitamins/Minerals | 1.00 |
| TOTAL | 100.00 |

Animal feeds were prepared by introducing a cereal carrier containing approximately 3 mg enzyme protein/kg into the wheat diet at a concentration of 1 kg of enzyme and carrier per tonne of wheat diet. The final concentration of enzyme protein in the feed was thus approximately 3 mg per tonne. The xylanase was obtained from *Trichoderma longibrachiatum*. Broiler chicks were fed the wheat plus xylanase diet from hatching. For comparison purposes, separate flocks of chicks were fed with the wheat diet and the maize diet without the addition of xylanase. A challenge model was used, whereby 0.2 ml of a stock solution of *C. jejuni* were introduced to each chick by syringe at day 7 from hatching. The dilution level of the stock solution was varied, from $10^{-1}$ (high challenge) to $10^{-6}$ (low challenge, similar to natural conditions). The undiluted stock solution contained approximately $10^4$ CFU per 0.2 ml. The caecae of the chicks were examined for damage due to the *Campylobacter* at varying ages.

Example 1

FIGS. 1–6 show the effect of the diets on *Campylobacter* colonisation in 12-day old chicks. In each case two flocks, A and B, were tested to minimise the effect of environmental variance on the results. In each case it is clearly evident that a wheat plus xylanase diet is effective in reducing the level of *Campylobacter* in the caecae of the chicks in comparison with a maize diet. Additionally, at *Campylobacter* stock solution dilution levels of $10^{-3}$ or lower (i.e. approaching more natural conditions), the wheat plus xylanase diet becomes considerably more effective than the wheat diet alone. Thus, in FIG. 1, for the wheat plus xylanase diet at a *Campylobacter* stock solution dilution of $10^{-6}$, a mean score of 0.5 positive caecae was observed. The equivalent scores for diets lacking xylanase were approximately 1.5 and 2.5.

Example 2

Figure 1:
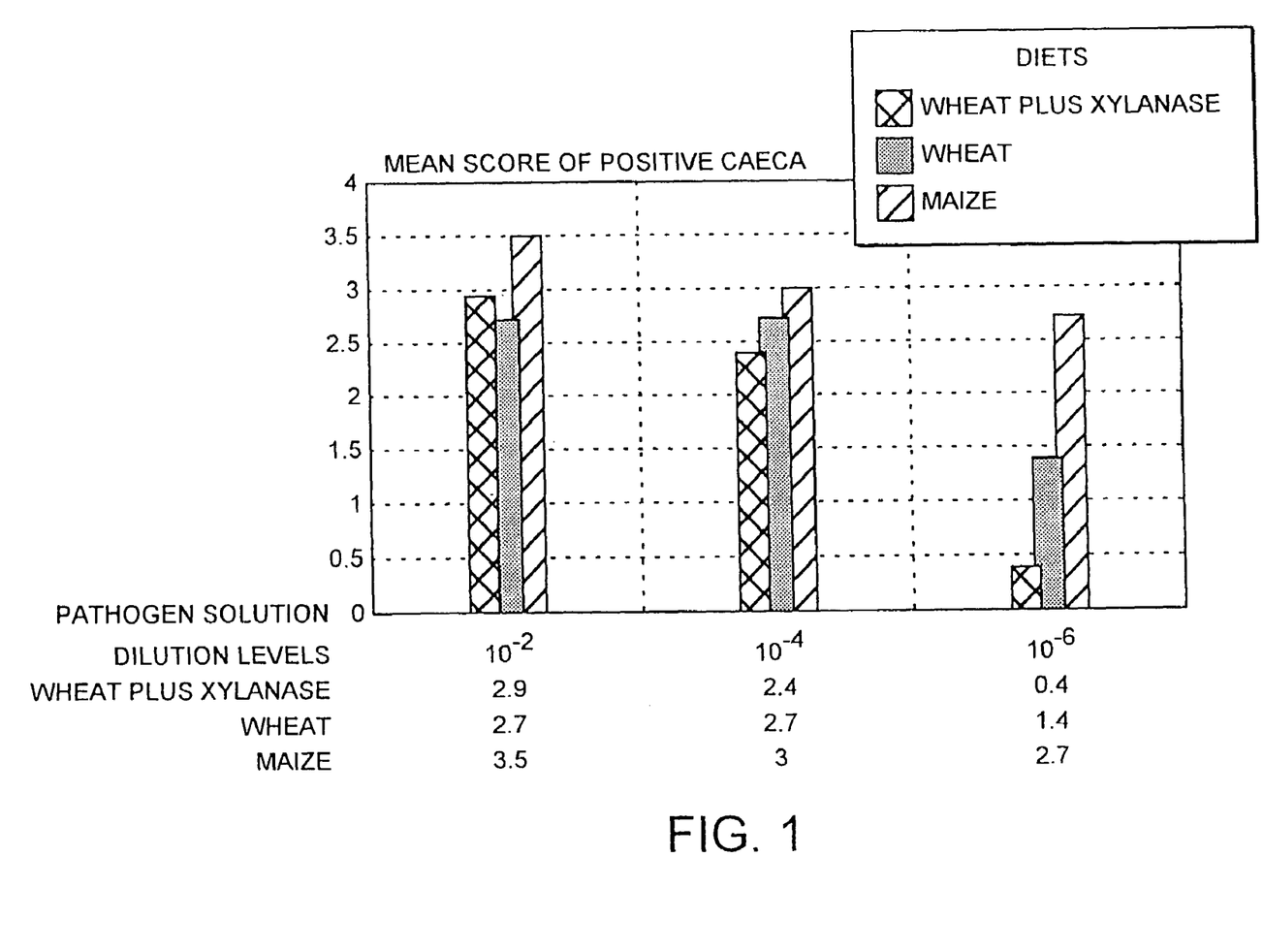
FIG. 1 shows the effect of three diets on *Campylobacter* colonisation in 12-day old chicks. Three different dilution levels of the initial stock solution of *Campylobacter* were used to introduce the pathogen to the chicks. The results are presented as mean scores of positive caecae and represent the combined results of two flocks A and B comprising a total of 108 birds (12 per dilution for each of the three diets).
Figure 2:
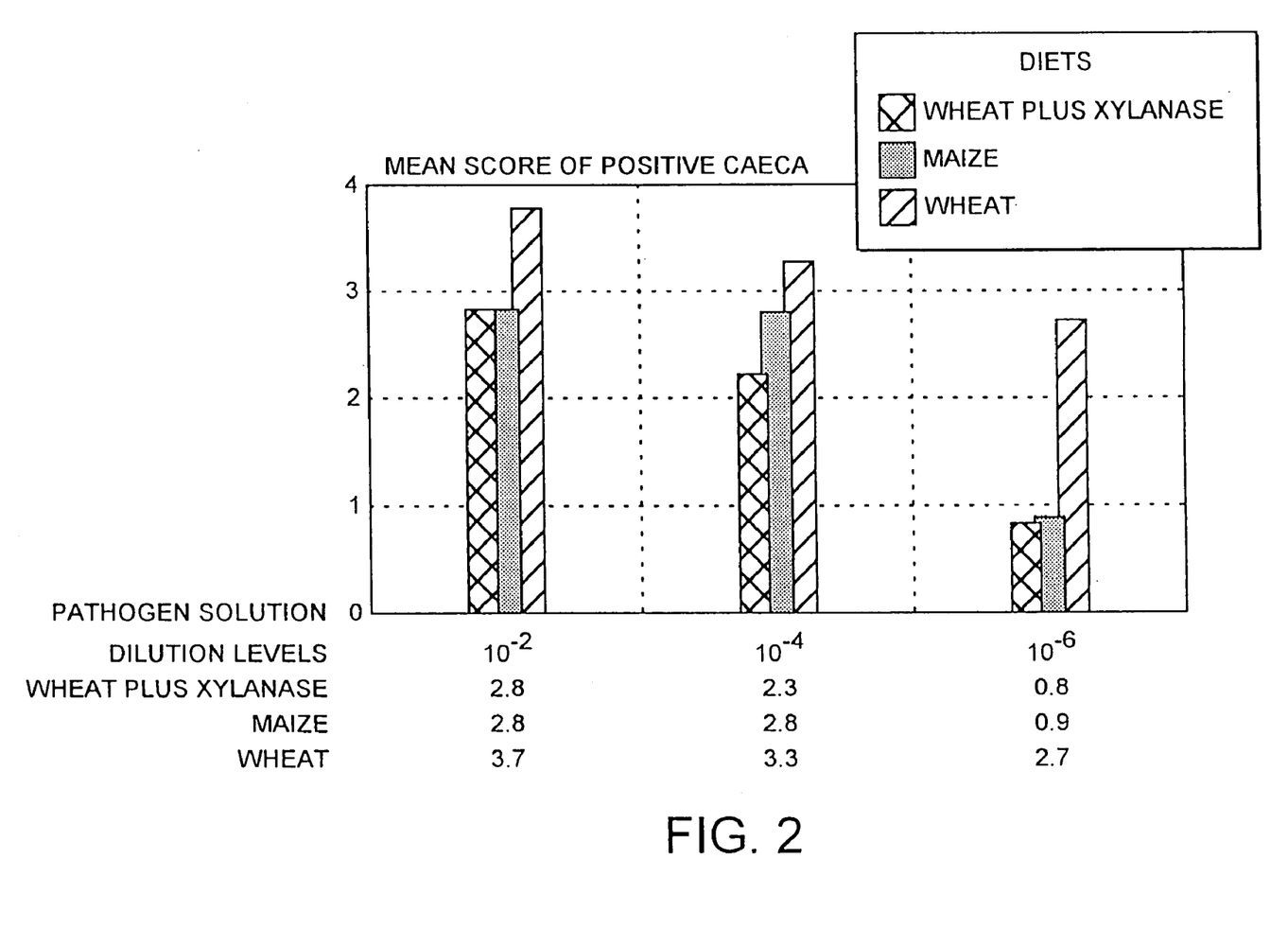
FIG. 2 shows the results of FIG. 1, but for flock A alone.
Figure 3:
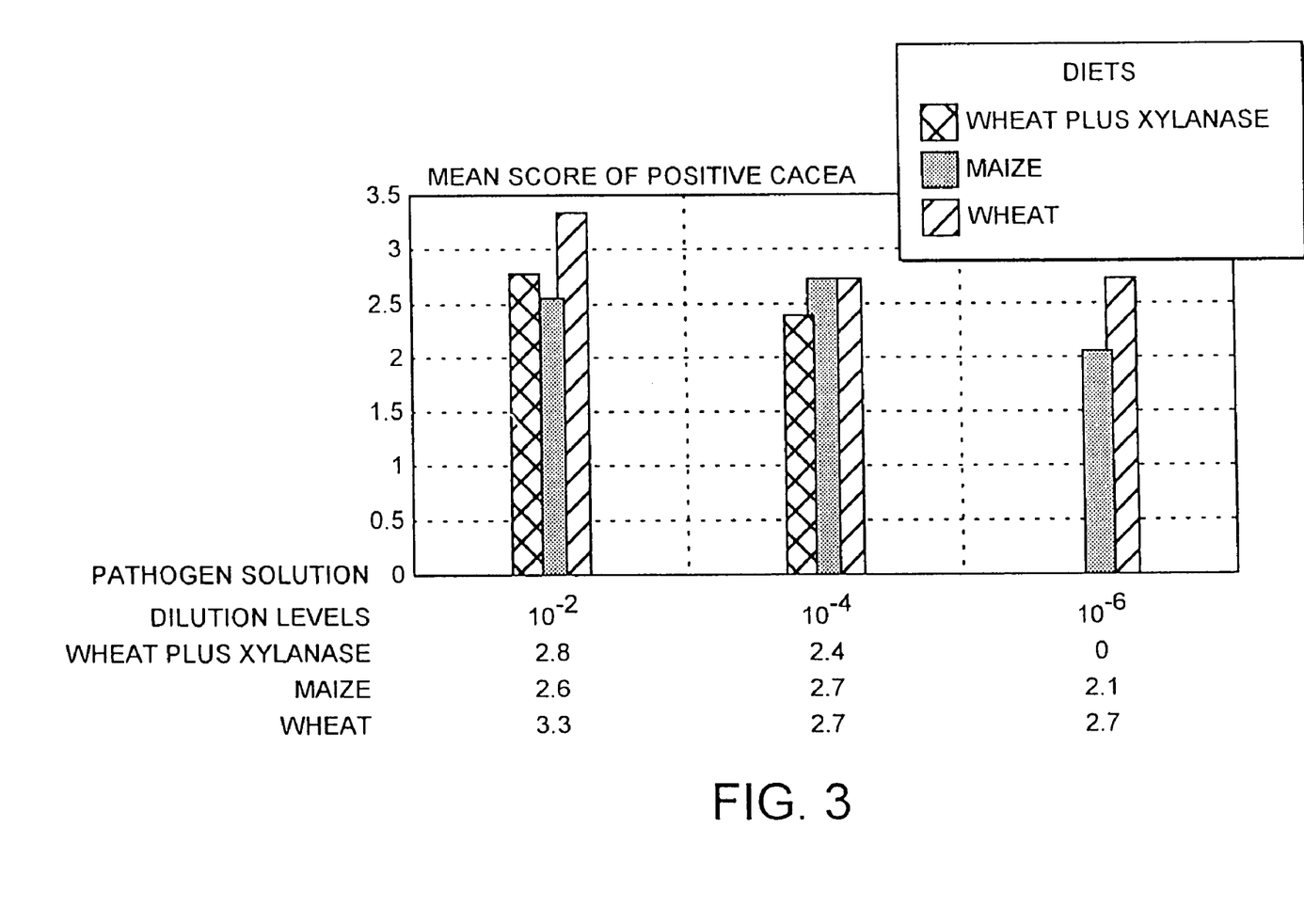
FIG. 3 shows the results of FIG. 1, but for flock B alone.
Figure 4:
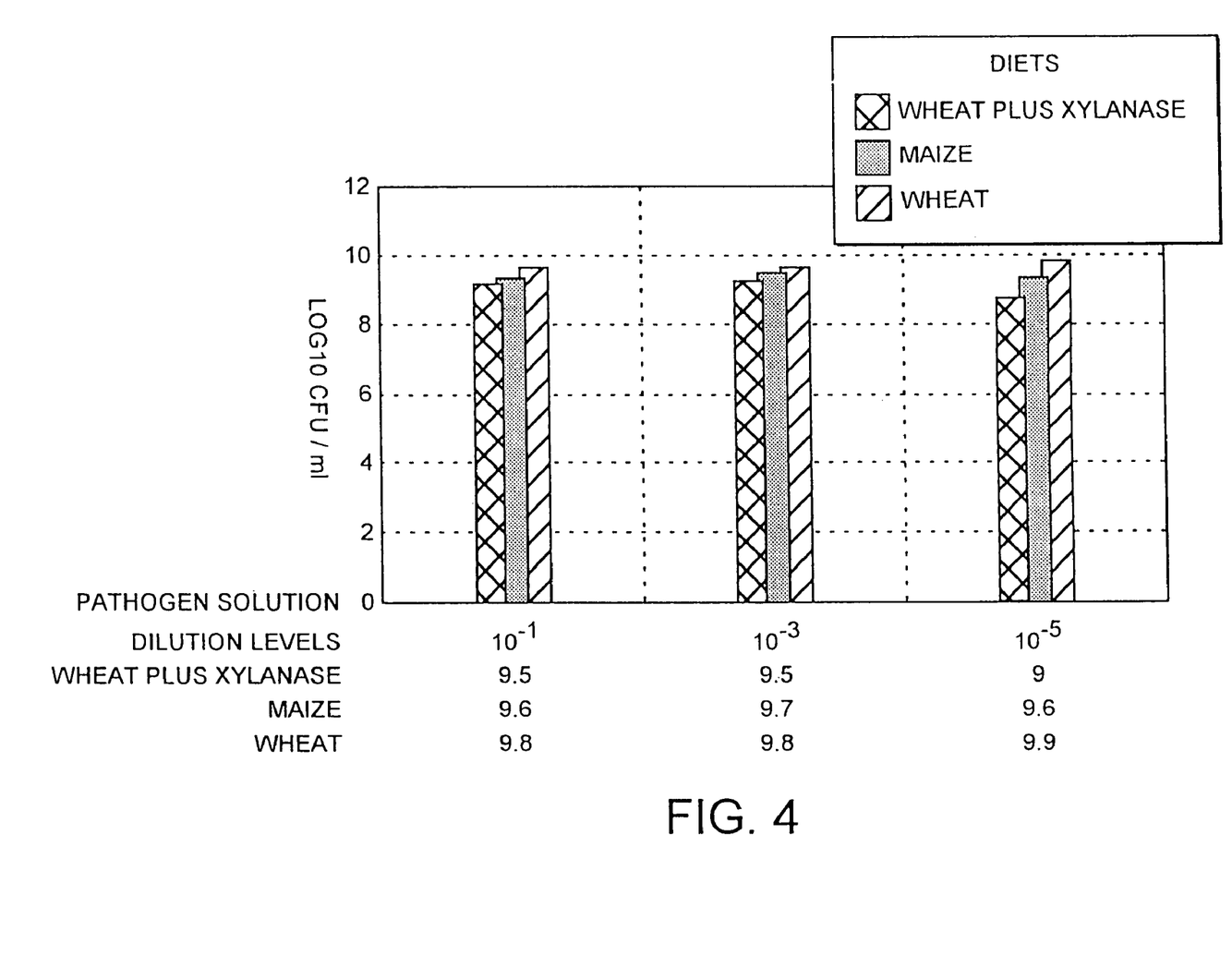
FIG. 4 shows similar results to FIG. 1, but at three alternative dilution levels of the initial *Campylobacter* stock solution. The results are presented as mean counts $\log_{10}$CFU (Colony Forming Units)/ml.
Figure 5:
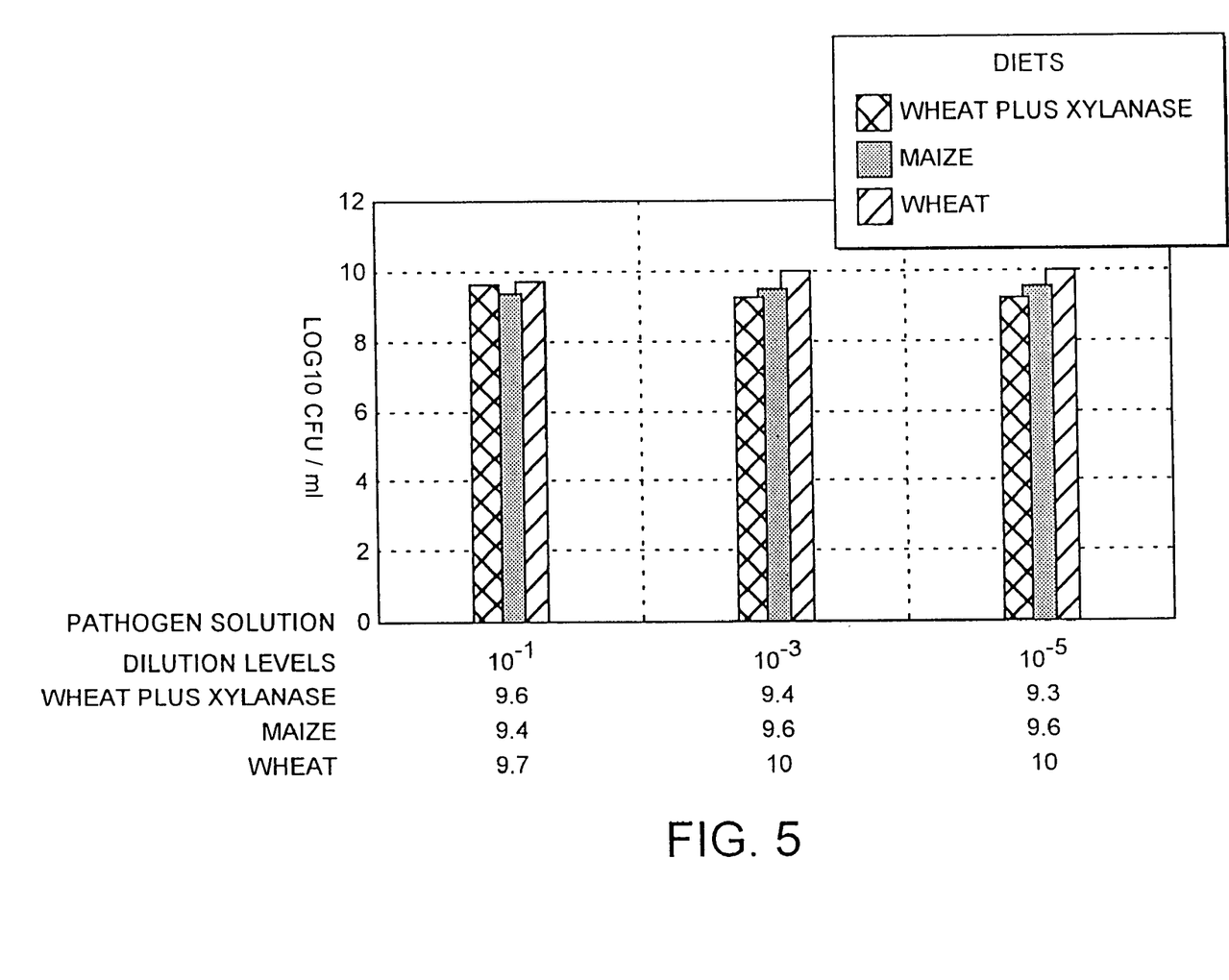
FIG. 5 shows the results of FIG. 4, but for flock A alone.
Figure 6:
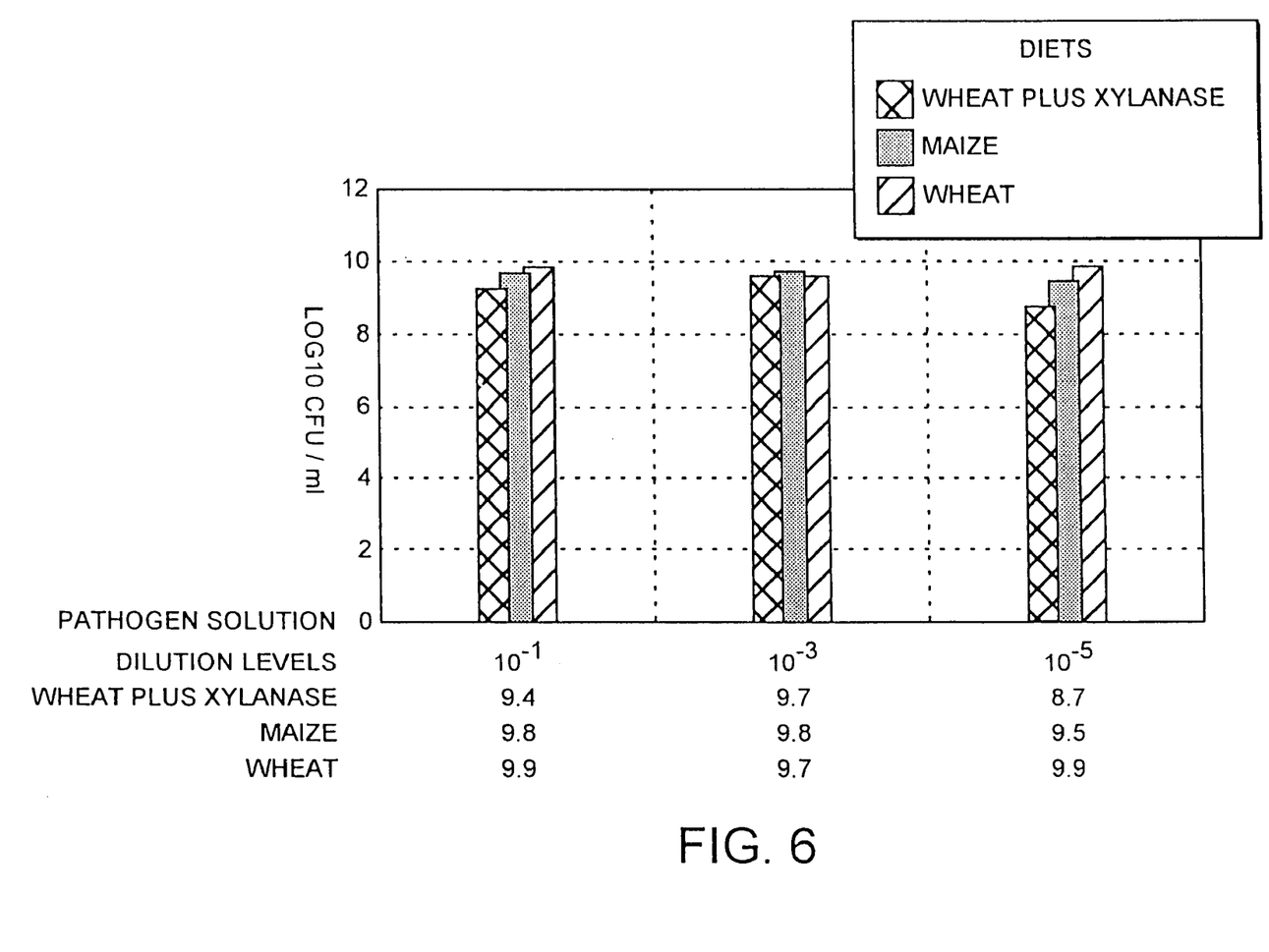
FIG. 6 shows the results of FIG. 4, but for flock B alone.
Figure 7:
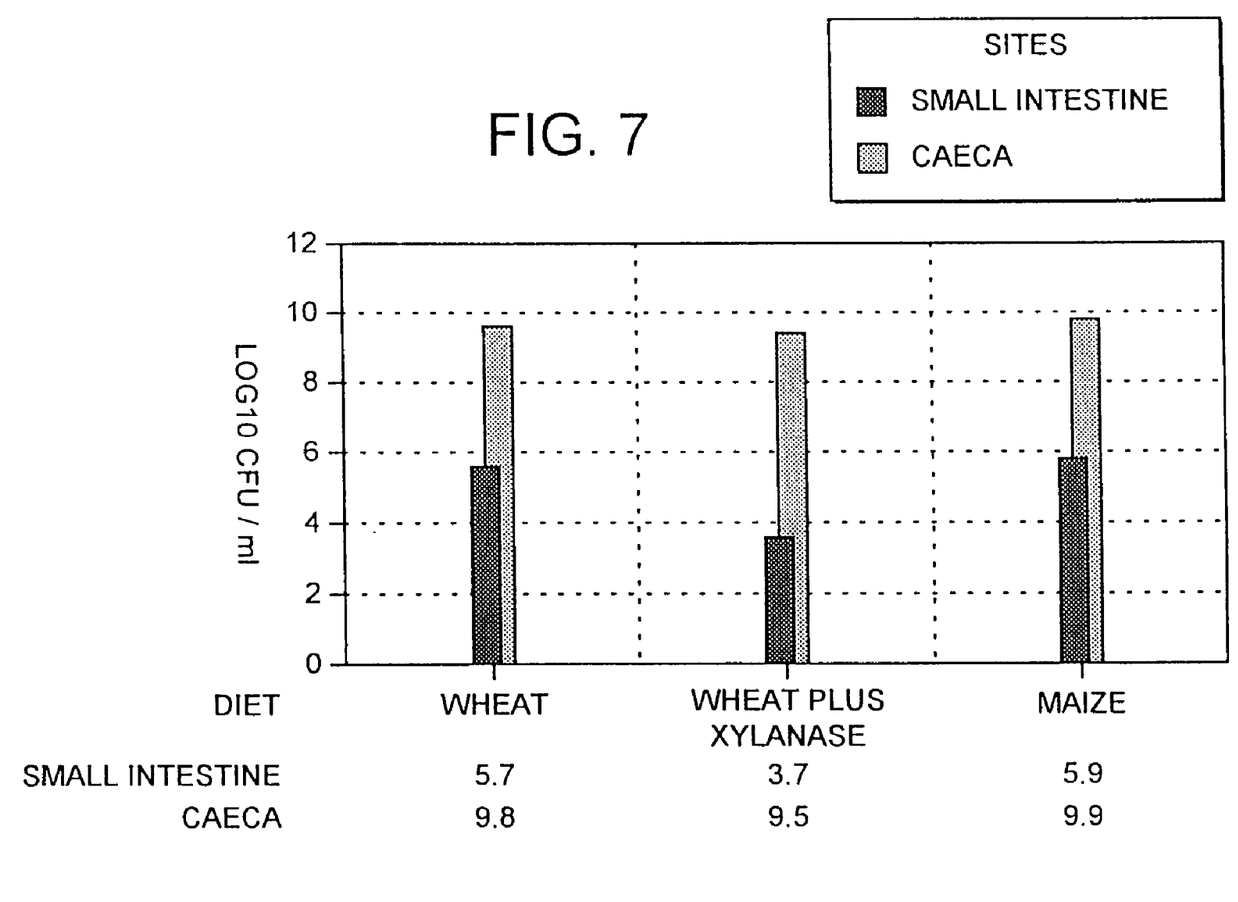
FIG. 7 shows the effect of three diets on *Campylobacter* colonisation of the small intestine and caecae of 17-day old chicks. The results are presented as mean counts $\log_{10}$CFU/ml, and represent the combined results of two flocks A and B comprising a total of 72 birds (12 per treatment) for each of the three diets.
Figure 8:
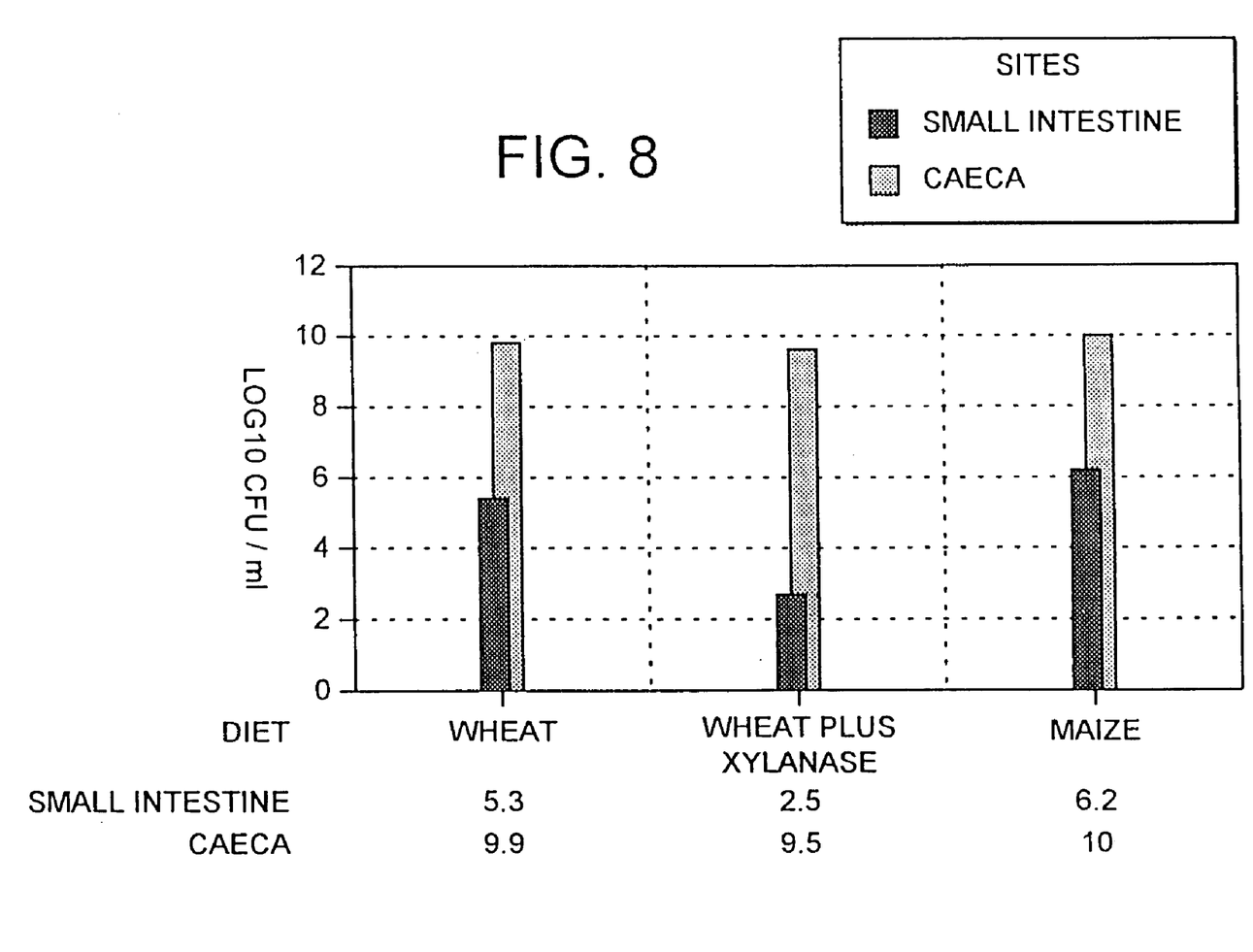
FIG. 8 shows the results of FIG. 7, but for flock A alone.
Figure 9:
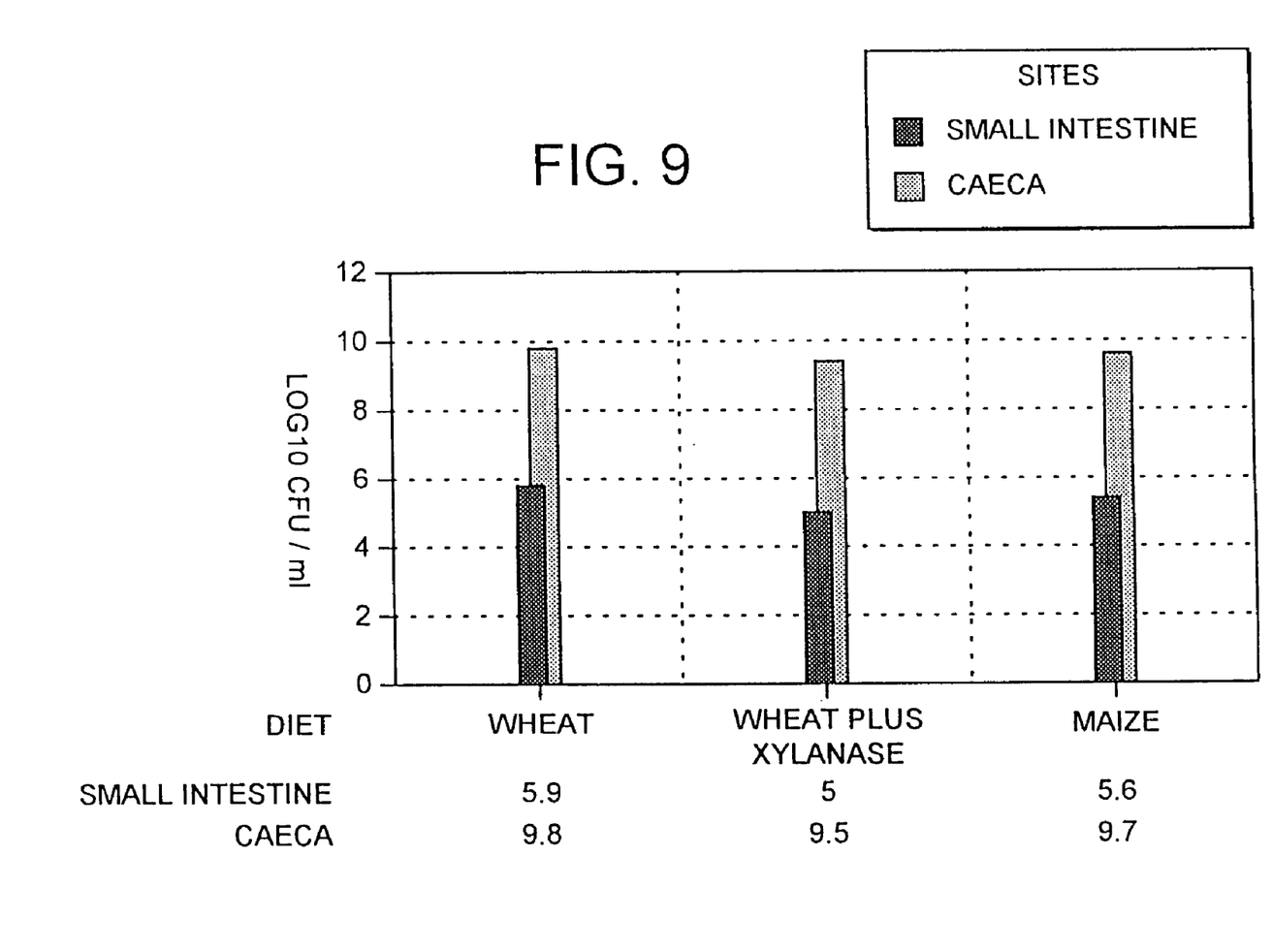
FIG. 9 shows the results of FIG. 7, but for flock B alone.

FIGS. 7–9 demonstrate the effectiveness of the diets on *Campylobacter* colonisation of the small intestine and caecae of 17-day old chicks from two flocks. The effect of the wheat plus xylanase diet on reducing the *Campylobacter* colonisation of the caecae of the chicks is evident as already demonstrated in Example 1. However this reduction is even more marked as regards the small intestine. Accordingly, in FIG. 7 the mean count $\log_{10}$CFU in the small intestine measured for chicks on the wheat and xylanase diet was less than 4. The equivalent counts for the diets not containing xylanase were found to be approximately 6, i.e. 100-fold higher.

Example 3

Figure 10:
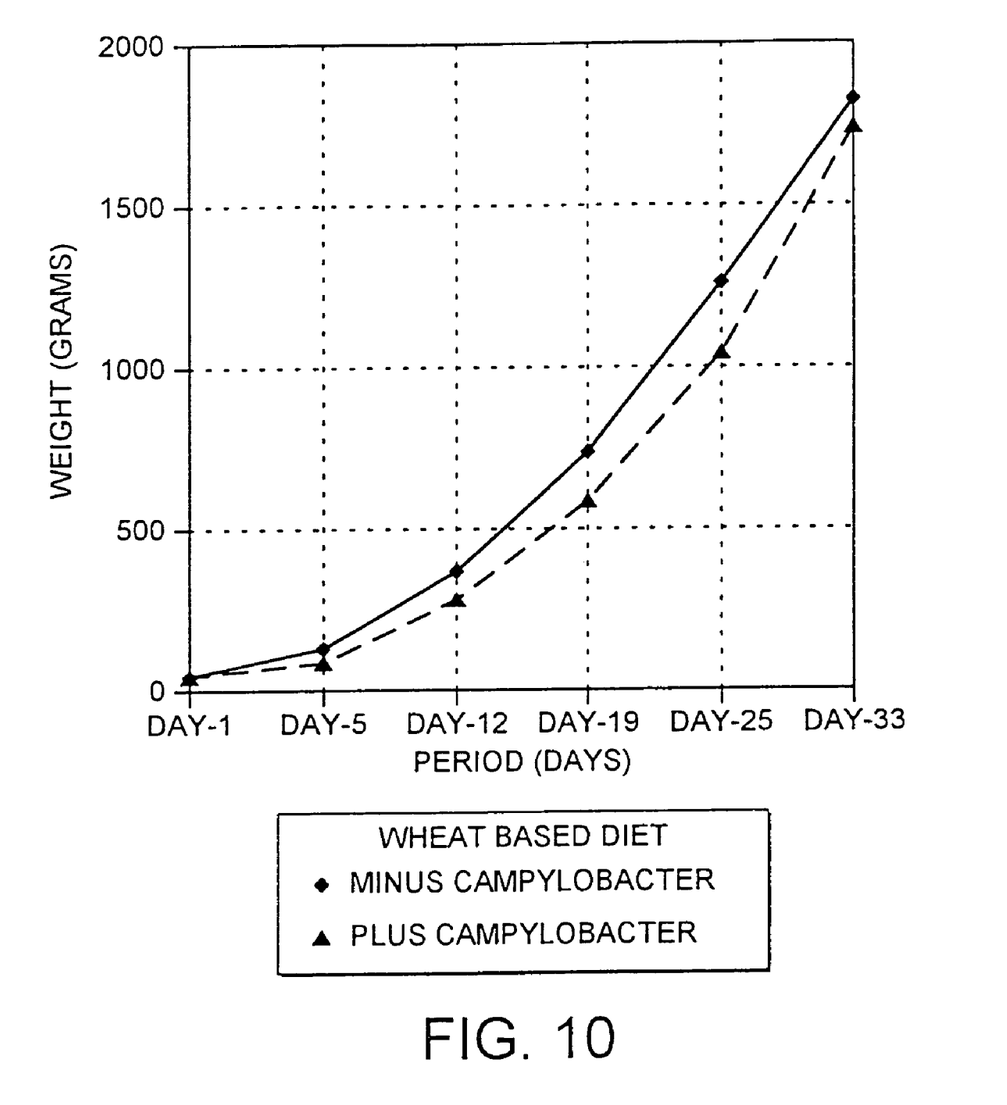
FIG. 10 shows a comparison of the weight of 1, 5, 12, 19, 25 and 33-day old chicks (20 in total) dosed with *Campylobacter jejuni*, and similar chicks (25 in total) which have not been dosed, the chicks all being fed a wheat-based diet.
Figure 11:
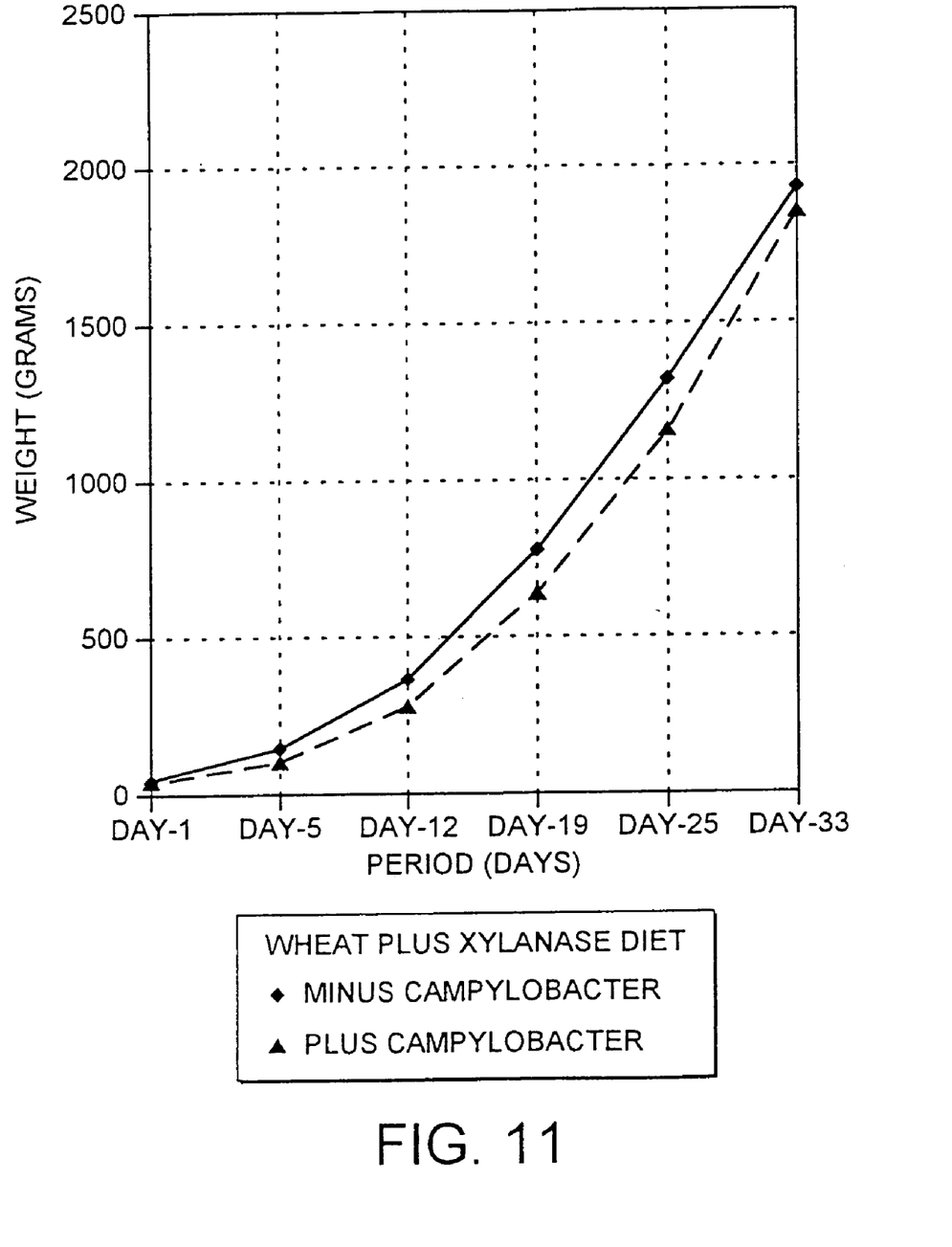
FIG. 11 shows similar results to those of FIG. 10, but for chicks on a wheat plus xylanase diet.
Figure 12:
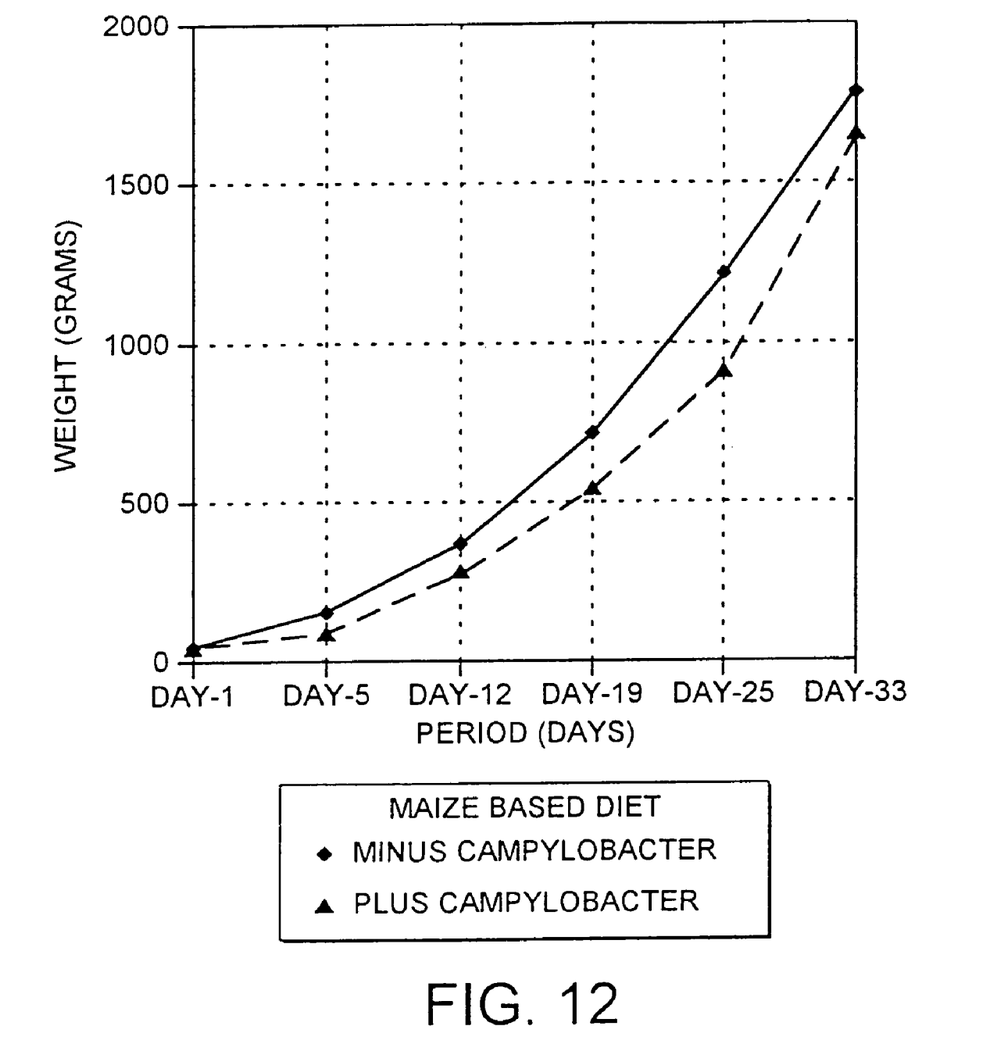
FIG. 12 shows similar results to those of FIG. 10, but for chicks on a maize-based diet.

FIGS. 10–12 depict a comparison of the effect of different diets on the weight of 1, 5, 12, 19, 25 and 33-day old chicks. FIG. 10 shows the results for the wheat-based diet, FIG. 11 the results for the wheat plus xylanase-based diet and FIG. 12 the results for the maize-based diet. The weight of the chicks in each case is reduced by dosing with *Campylobacter*. However, those chicks to which *Campylobacter* has been introduced gain weight more quickly on the wheat plus xylanase diet than on either of the other diets.

Example 4

Figure 13:
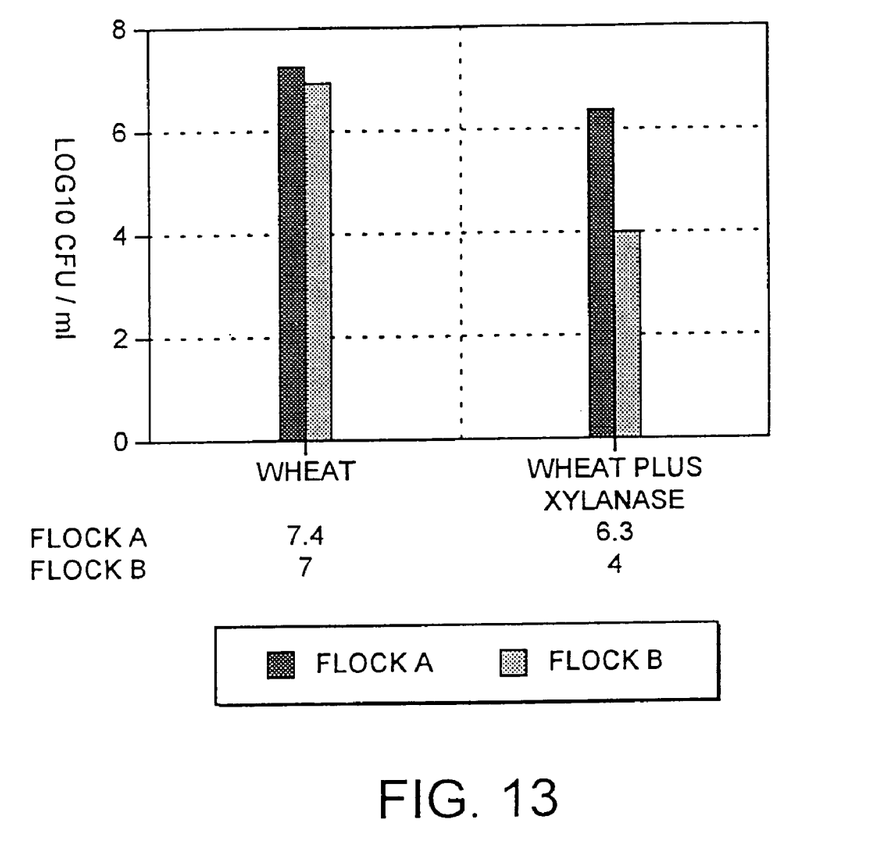
FIG. 13 shows the effect of two different diets (wheat and wheat plus xylanase) on *Salmonella enteritidis* colonisation in 14 day old chicks. The results are presented as mean counts $\log_{10}$CFU/ml. Tests were carried out on two flocks, A and B, comprising a total of 48 birds, 24 per diet.

FIG. 13 demonstrates the effectiveness of the wheat and wheat plus xylanase diets on *Salmonella enteritidis* colonisation of the caecae of 14-day old chicks from two flocks, A and B. The methodology employed in these experiments was identical to that employed for the *Campylobacter* experiments described above, except that the undiluted stock solution of *Salmonella enteritidis* contained approximately $10^5$ CFU per 0.2 ml. The effect of the wheat plus xylanase diet on reducing the *Salmonella* colonisation of the caecae of the chicks is clearly evident. Thus, in flock B, the chicks on the wheat diet were found to have a mean count $\log_{10}$CFU/ml of approximately 7. However, the chicks from flock B on the wheat plus xylanase diet were found to have a much lower $\log_{10}$CFU/ml of approximately 4 (1000-fold lower).

The above Examples clearly show a reduction in bacterial infection in the gut due to the inclusion of xylanase in the diet. Similar results have been observed when using a cellulase such as a β-glucanase. This indicates that the use provided by the present invention significantly reduces the ability of certain bacteria to colonise the caecae which in turn prevents migration of the bacteria to the small intestine. Accordingly, since it has a reduced level of infection, the growth rate of the animal is increased, leading to economic benefits. The reduction in contamination rate also has obvious benefits to human health and the replacement of antibiotics by such diets has clear environmental benefits.

The invention claimed is:

1. A method for treatment of bacterial infection in chickens having bacterial infection in the absence of therapeutic amounts of antimicrobial drugs, the bacterial infection caused by bacteria selected from the group consisting of *Salmonella, Campylobacter, Clostridium perfringens*, and mixtures thereof, the method comprising:

feeding the chickens a diet which diet is effective for treatment of bacterial infection in chickens caused by bacteria selected from the group consisting of *Salmonella, Campylobacter, Clostridium perfringens*, and mixtures thereof, the diet including xylanase with the xylanase being present in an amount effective for treatment of the bacterial infection in the absence of an antimicrobial drug or in the presence of an antimicrobial drug at a concentration that in the absence of the xylanase is not effective for treatment of bacterial infection in chickens caused by bacteria selected from the group consisting of *Salmonella, Campylobacter, Clostridium perfringens*, and mixtures thereof, and the diet not containing an antimicrobial drug or containing an antimicrobial drug at a concentration that is not effective in the absence of the xylanase for treatment of bacterial infection in chickens caused by bacteria selected from the group consisting of *Salmonella, Campylobacter, Clostridium perfringens*, and mixtures thereof.

2. The method according to claim 1 wherein the xylanase is mixed with a feed to form a xylanase/feed mixture.

3. The method according to claim 2 wherein the xylanase is fed to the chickens in an amount of about 0.0001 to about 10 grams of xylanase per kg of xylanase/feed mixture.

4. The method according to claim 2 wherein the xylanase is fed to the chickens in an amount of about 0.001 to about 1 gram of xylanase per kg of xylanase/feed mixture.

5. The method according to claim 2 wherein the xylanase is fed to the chickens in an amount of about 0.01 to about 0.1 gram of xylanase per kg of xylanase/feed mixture.

6. The method according to claim 2 wherein the xylanase/feed mixture comprises at least about 25% by weight of a cereal selected from the group consisting of wheat, maize, rye, barley, oats, triticale, rice, sorghum and mixtures thereof.

7. The method according to claim 6 wherein the cereal is wheat.

8. The method according to claim 1 wherein the xylanase is obtained from a fungus selected from the group consisting of *Trichoderma, Aspergillus, Humicola, Neocallimastix*, and mixtures thereof.

9. The method according to claim 1 wherein the xylanase is obtained from a bacteria selected from the group consisting of *Bacillus, Strepomyces, Clostridium, Ruminococcus*, and mixtures thereof.

10. The method according to claim 1 wherein the diet is fed to the chickens without a withdrawal period prior to slaughtering of the chickens.

11. The method according to claim 1 wherein said diet does not contain an antimicrobial drug.

12. The method according to claim 1 wherein said diet contains an antimicrobial drug at a concentration that is not effective for treatment and/or prophylaxis of bacterial infection in chickens caused by bacteria selected from the group consisting of *Salmonella, Campylobacter, Clostridium perfringens*, and mixtures thereof in the absence of the xylanase.

13. The method according to claim 10 wherein said diet does not contain an antimicrobial drug.

14. The method according to claim 10 wherein said diet contains an antimicrobial drug at a concentration that is not effective for treatment and/or prophylaxis of bacterial infection in chickens caused by bacteria selected from the group consisting of *Salmonella, Campylobacter, Clostridium perfringens*, and mixtures thereof in the absence of the xylanase.

15. A method for treating a bacterial infection in a chicken caused by bacteria selected from the group consisting of *Salmonella, Campylobacter, Clostridium perfringens*, and mixtures thereof, the method comprising:

feeding the chicken an animal feed comprising xylanase in an amount effective for treating the bacterial infection.

* * * * *